ns Patent [19]

Chauvin et al.

[11] 4,207,249
[45] Jun. 10, 1980

[54] CATALYTIC PROCESS FOR SYNTHESIZING METHANE BY REACTING HYDROGEN WITH CARBON MONOXIDE

[75] Inventors: Yves Chauvin, Le Peca; Dominique Commereuc, Meudon; Igor Tkatchenko, Caluire, all of France

[73] Assignee: Institut Francais du Petrole, Rueil-Malmaison, France

[21] Appl. No.: 960,395

[22] Filed: Nov. 13, 1978

[51] Int. Cl.² .......................... C07C 1/04; C07C 1/06
[52] U.S. Cl. ..................... 260/449.6 M; 260/449.6 R; 260/449 L

[58] Field of Search ................... 260/449.6 M, 449 M, 260/449 L

[56] References Cited

U.S. PATENT DOCUMENTS 3,989,734  11/1976  Alpert et al. ................. 260/449.6 M Primary Examiner—Howard T. Mars
Attorney, Agent, or Firm—Millen & White

[57] ABSTRACT

Methane is manufactured by reacting hydrogen with carbon monoxide in an inert liquid medium comprising a catalyst obtained by reacting a nickel compound with a reducing aluminum compound.

9 Claims, No Drawings

CATALYTIC PROCESS FOR SYNTHESIZING METHANE BY REACTING HYDROGEN WITH CARBON MONOXIDE

The object of the present invention is a process for producing methane from hydrogen and carbon monoxide.

It has long been known that methane may be obtained with high selectivity by contacting carbon monoxide and hydrogen with a nickel-based catalyst. This reaction has been particularly used up to now for removing low amounts of carbon monoxide from hydrogen, as obtained by steam-reforming or by partial oxidation of a hydrocarbon fraction.

Now, in view of a possible energy shortage, manufacture of methane as substitute of natural gas has gained interest.

The main difficulty encountered when reacting carbon monoxide with hydrogen is the transfer of heat released by this strongly exothermic reaction.

The conventional use of heterogeneous catalysts in fixed bed is not favourable to efficient heat exchange, and this can lead to spot overheatings which are detrimental to the activity and life of the catalyst. The technique of suspending heterogeneous catalyst in a nonvolatile liquid phase could be used in that case. This technique has been prior disclosed, for example in U.S. Pat. No. 3,989,734.

This technique, although more effective for heat exchange, results however in a yield decrease, due to an insufficient diffusion of the reactants towards the catalyst as consequence of the presence of the liquid phase.

The present invention makes use of a catalyst system which avoids the above disadvantages. This catalyst system is produced by admixing and reacting two constituents A and B in an inert liquid medium which may be used thereafter as reaction medium or as constituent of the reaction medium.

The constituent A of the catalyst is a nickel compound. The following nickel compounds are convenient, although their list is not limitative: nickel chloride, nickel bromide, nickel iodide, nickel acetylacetonate, nickel acetate, nickel oxalate, nickel formate and, as a rule, nickel carboxylates. Preference is given to nickel carboxylates derived from fatty acids comprising 6 to 20 carbon atoms, or more; for example, a mixture of carboxylates of fatty acids with 8, 9 and 10 carbon atoms, in view of their high solubility in hydrocarbon media. Examples thereof are nickel octoate, stearate and oleate.

The constituent B of the catalyst is an aluminum reducing compound of the general formula $AlR_3$, wherein at last one of the R radicals is a monovalent hydrocarbon radical, the other radicals being selected from hydrogen, monovalent hydrocarbon radicals and/or alkoxy radicals. A trialkylaluminum compound is preferred, for example, trimethylaluminum, triethylaluminum or triisobutylaluminum. The monovalent hydrocarbon radical and the alkoxy radical preferably comprise 1 to 6 carbon atoms.

The liquid medium in which the two constituents A and B are admixed is preferably used thereafter as reaction medium or component of this reaction medium. It must exhibit both chemical inertness and heat stability. Good results in this respect are obtained with saturated hydrocarbons, particularly paraffinic hydrocarbons, liquid in the reaction conditions, for example, with heptane, octane, dodecane, hexadecane or mixtures of these hydrocarbons, for example cuts of oils or liquid paraffins, after removal of the catalyst poisons, when necessary.

The catalyst may also be prepared in a liquid medium different from that used subsequently as liquid reaction medium. In that case, this liquid medium may be relatively volatile without disadvantage, and it may be removed during the methanation step.

The invention is not limited to the use of a particular reaction medium. All those disclosed in the literature and patents may be used, provided they are compatible with the catalyst and sufficiently stable in the reaction conditions.

The two constituents A and B of the catalytic system are usefully admixed in such proportions that the atomic aluminum/nickel ratio be from 1:1 to 20:1. Preferred ratios are from 2:1 to 10:1.

The catalyst is prepared by admixing constituent A with constituent B in an inert liquid medium, the reactants being admitted in admixture or separately in any order. A preferred embodiment is given hereunder.

Constituent A of the catalyst is dissolved or suspended in a paraffinic solvent previously free from air, this operation being carried out in an inert nitrogen or argon atmosphere, or in a hydrogen atmosphere. The aluminum constituent B is then slowly added, itself under inert or reducing atmosphere. The admixing results in gas release and strong heat release, which limits the rate of addition of the constituent B. It is preferred that, during this manufacture, the temperature of the reaction mixture be kept in the range from 0° to 200° C., and advantageously from 20° to 100° C.

The admixing step may be effected either directly in the methanation reactor or, more easily, in a glass laboratory vessel. The mixture is then transferred into the reactor, in a further step, while avoiding air and humidity access. Traces of air or humidity may, however, in certain cases, be harmless or have a co-catalytic effect.

The catalyst thus obtained appears as a dark brown solution of homogeneous appearance which may be circulated through a pump, for example, when transferring it into the reactor.

The substantial homogeneity of the catalyst solution guarantees both good thermal diffusion, thus efficient removal of the reaction heat, and good chemical diffusion, i.e. good accessibility of the reactants to the catalyst. These two conditions were not simultaneously met by the catalysts of the prior art.

The composition of the synthesis gas mixture, expressed as the molar ratio of hydrogen to carbon monoxide is usefully from 1:1 to 6:1. The preferred ratio is about 3:1, corresponding to the theoretical stoichiometry of the reaction.

The pressure of the synthesis hydrogen/carbon monoxide mixture may vary from atmospheric pressure up to 50 bars or more, although a pressure of 1–20 bars is preferred.

The hourly space velocity, expressed as volumes of synthesis gas mixture in standard conditions, per volume of reactor and per hour (VVH) may be chosen from 1 to 5,000. Preferred VVH is 50–1,000, for example, 50–200.

The reaction temperature may range from 100° to 450° C., preferably 250°–350° C. The lower limit depends partly on the selected hydrogen/carbon monoxide ratio and the pressure. It is indeed preferred to select operating conditions outside of the nickel tetracarbonyl stability range. It is usually operated at a temperature above this stability range, corresponding to a temperature about 200° C. when operating at a hydrogen/carbon monoxide ratio of 3:1 and a pressure of about 10 bars.

For this reason, it is preferred, when heating or stopping the reactor, to scavenge it with a carbon monoxide-free gas mixture, such as pure hydrogen.

The following examples illustrate the present invention and are not to be considered as limiting it in any respect. Results obtained with conventional catalysts are also given by way of comparison.

The reactor used in the following experiments was part of a micropilot unit for continuous operation. The reactor comprises a stainless steel pipe of 2 cm internal diameter and 100 cc capacity. It is half filled with a catalyst solution to which pure solvent has been added in certain cases. The synthesis gas mixture is injected from the bottom of the reactor through a fritted injector permitting diffusion throughout the reaction mixture whose volume thus increases. The gas is passed through a separator where liquid fractions can settle, when present, and is then expanded and collected in a gas-holder for subsequent analysis. No recycling is provided for, to simplify the experiment. However, in certain cases, at least partial recycling may be helpful to ensure a more complete conversion of the reactants.

EXAMPLE 1

10.6 g of a mixture of $C_8$–$C_{10}$ nickel carboxylates with an average nickel content of about 11% by weight is introduced into a 250 cc glass vessel in argon atmosphere. 50 cc of paraffin oil previously freed from gas at 80° C. in vacuo is then added and the contents are stirred at room temperature to completely dissolve the nickel salt. 7 cc of triethylaluminum is then slowly added by means of a syringe, which corresponds to an atomic ratio of aluminum to nickel of 2.5:1. Heating developed through the reaction is moderated by immersing the vessel into a water bath, which maintains the temperature of the mixture below 50° C. The solution turns rapidly dark brown and exhibits a homogeneous aspect. After addition of triethylaluminum, the catalytic solution is transferred into the steel reactor, as hereinbefore described, in argon atmosphere.

A synthesis gas of $H_2/CO$ ratio of 3.8:1 by volume is injected at a rate of 17.2 liters per hour. The pressure in the reactor is 8 bars and the initial temperature of 330° C. stabilizes at 345° C. as consequence of the reaction heat release. During 8 hours of run, the average hydrocarbon content of the effluent gas is 31% by volume. The hydrocarbon composition by weight is: methane: 90.8%; ethane: 6.1%; propane: 1.7%; butanes: 1.4%

The % molar conversion defines as:

$$\% C = \frac{CH_4 + 2C_2H_6 + 3C_3H_8 + 4C_4H_{10} + CO_2}{CO \text{ (inlet)}} \times 100$$

is 61.9%.

The % molar methane selectivity defed as:

$$\% S = \frac{CH_4}{CH_4 + 2C_2H_6 + 3C_3H_8 + 4C_4H_{10} + CO_2} \times 100$$

is 84.6%.

The productivity, showing the catalyst performance, expressed as liters of gaseous hydrocarbons produced per gram of nickel metal and per hour, is 1.95 liters/g/hour.

EXAMPLE 2

An additional 8-hour run is effected, following that of Example 1, after stopping of the reactor overnight. The synthesis gas whose $H_2/CO$ ratio is 3.8:1 by volume is injected at a rate of 16.5 l/h. The pressure is maintained at 8 bars and the temperature slowly increases from 315° to 345° C. throughout the run. The average hydrocarbon content of the effluent gas is 46% by volume. The composition of these hydrocarbons, in % by weight, is: methane: 95.2%; ethane: 3.4%; propane: 0.9%; butanes: 0.5%.

The conversion, selectivity and productivity, as defined in Example 1, are:
C=79.0%
S=82.8%
P=2.3 l/g/h.

EXAMPLE 3

This example describes an experiment conducted with a catalyst of the prior technique and is given by way of comparison.

50 g of catalyst of about 10% nickel content on alumina balls are charged into the reactor used in the above examples, although arranged for downwardly passing the synthesis gas. This catalyst is activated by passing hydrogen at 350° C., 10 bars pressure and a rate of 70 l/h for 8 hours. After this activation phase, hydrogen is substituted with synthesis gas of composition $H_2/CO=3/1$ injected at a rate of 37.9 l/h. The pressure is 7 bars in the reactor and the temperature remains at 360° C. for the 7 hours of the run. The average hydrocarbon content of the effluent gas is 80.5% by volume. The composition of these hydrocarbons, in % b.w., is: methane: 98.3%; ethane: 0.9%; propane: 0.8%.

The conversion, selectivity and productivity, as defined in Example 1, are:
C=59.5%
S=82.1%
P=0.93 l/g/h.

EXAMPLE 4

This example illustrates the use of a crushed catalyst suspended in a liquid phase, according to the prior technique, and is given by way of comparison. 10 g of the catalyst of Example 3 are finely crushed to powder and introduced into the reactor used in the preceding examples, also arranged with an inlet for the synthesis gas at the bottom and an outlet for the product at the top. The powdered catalyst is activated by means of hydrogen at 15 bars and 300° C. for 8 hours. 40 cc of paraffin oil of the same type as used in examples 1 and 2 is then injected through a pump into the reactor. A synthesis gas of composition $H_2/CO$: 4.4/1 is injected at a rate of 20 l/h. The reactor pressure is 8 bars and the temperature stabilizes at 345° C. The average hydrocarbon content of the effluent gas is 11.5% by volume. The composition of these hydrocarbons in % by weight is as follows: methane: 82.1%; ethane: 7.8%; propane: 8.9%; butanes: 1.2%.

The conversion, selectivity and productivity, as defined in example 1, are:
C=44.8%
S=81.1%
P=1.49 l/g/h.

EXAMPLE 5

A new sample of the catalyst solution is prepared according to the method of example 1. However, the amounts of nickel carboxylate and triethylaluminum are such that the catalyst solution contains the equivalent of 2.3 g nickel metal with an atomic ratio aluminum/nickel of 3/1.

This catalytic solution is transferred into the steel reactor under inert pressure.

A synthesis gas of ratio $H_2/CO = 3.1/1$ by volume is then injected at a rate of 43.2 l/h. The pressure in the reactor is 25 bars and the temperature remains at 300° C. During 10 hours of continuous run, the average hydrocarbon content of the effluent gas is 89.5% by volume. The composition of these hydrocarbons, in % b.w., is: methane: 98.7%; ethane: 1.1%; propane: 0.1%; butanes: 0.1%.

The conversion, selectivity and productivity, as defined in example 1, are:
C=100%
S=94.5%
P=4.7 l/g/h.

EXAMPLE 6

A new 10-hour run is effected, subsequent to that of Example 5, after having stopped the reactor overnight. The synthesis gas of ratio $H_2/CO = 3.1/1$ by volume is injected at rate of 20 l/h. The pressure is 10 bars and the temperature remains at 300° C. The average hydrocarbon content of the gas effluent is 88% by volume. The composition of the hydrocarbons in % by weight is: methane: 99.5%; ethane: 0.4%; propane: 0.1%.

The conversion, selectivity and productivity, as defined in example 1 are:
C=100%
S=90.8%
P=2.1 l/g/h.

What we claim is:

1. A process for manufacturing methane by reacting hydrogen with carbon monoxide in an inert, liquid saturated hydrocarbon medium, in the presence of a catalyst, wherein the catalyst is prepared by reacting at least one nickel compound with at least one reducing aluminum compound in an inert liquid medium; wherein the aluminum compound has the formula $AlR_3$, at least one of the radicals R being a monovalent hydrocarbon radical, and the other radicals R being selected from hydrogen, monovalent hydrocarbon radicals and alkoxy groups; wherein the atomic ratio of aluminum of the aluminum compound to nickel of the nickel compound is from 1:1 to 20:1; and wherein the reaction of hydrogen with carbon monoxide is effected at a temperature of 100°–450° C. and a pressure of 1–50 bars.

2. A process according to claim 1, wherein the aluminum compound is a trialkylaluminum.

3. A process according to claim 1, wherein the nickel coumpound is a nickel carboxylate of a fatty acid with 6-20 carbon atoms.

4. A process according to claim 1, wherein the inert liquid medium comprises at least one saturated hydrocarbon.

5. A process according to claim 1, wherein the temperature is higher than the temperatures at which nickel carbonyl is stable.

6. A process according to claim 1, wherein the hydrogen and carbon monoxide are introduced into the reaction in the form of a synthesis gas mixture having a ratio of hydrogen to carbon monoxide of from 1:1 to 6:1.

7. A process according to claim 1, wherein the reaction is effected at a temperature of from 250°–350° C.

8. A process according to claim 1, wherein the reaction is effected at an hourly space velocity (VVH) of from 1 to 5,000.

9. A process according to claim 1, wherein the catalyst is prepared at a temperature of from 0° to 200° C.

* * * * *